United States Patent
Sgroi, Jr. et al.

(10) Patent No.: US 10,987,107 B2
(45) Date of Patent: Apr. 27, 2021

(54) SURGICAL STAPLING DEVICE

(71) Applicant: Covidien LP, Mansfield, MA (US)

(72) Inventors: Anthony Sgroi, Jr., Wallingford, CT (US); Charles R. Kollar, West Hartford, CT (US); David E. Valentine, Jr., East Hampton, CT (US); Joseph M. Guerrera, Watertown, CT (US)

(73) Assignee: Covidien LP, Manfield, MA (US)

( * ) Notice: Subject to any disclaimer, the term of this patent is extended or adjusted under 35 U.S.C. 154(b) by 215 days.

(21) Appl. No.: 16/010,614

(22) Filed: Jun. 18, 2018

(65) Prior Publication Data

US 2019/0008518 A1 Jan. 10, 2019

Related U.S. Application Data

(60) Provisional application No. 62/528,556, filed on Jul. 5, 2017.

(51) Int. Cl.
*A61B 17/115* (2006.01)
*A61B 17/064* (2006.01)
(Continued)

(52) U.S. Cl.
CPC ........ *A61B 17/1155* (2013.01); *A61B 17/068* (2013.01); *A61B 17/0643* (2013.01);
(Continued)

(58) Field of Classification Search
CPC ............ A61B 17/1155; A61B 17/0643; A61B 17/068; A61B 17/07207; A61B 17/07292;
(Continued)

(56) References Cited

U.S. PATENT DOCUMENTS 3,193,165 A 7/1965 Akhalaya et al.
3,388,847 A 6/1968 Kasulin et al.
(Continued)

FOREIGN PATENT DOCUMENTS

CA 908529 A 8/1972
CA 2805365 A1 8/2013
(Continued)

OTHER PUBLICATIONS

European Search Report dated Mar. 19, 2019, issued in EP Appln. No. 18181614.

*Primary Examiner* — Michelle Lopez

(57) ABSTRACT

A surgical stapling device includes a tool assembly having an anvil assembly and a staple cartridge, the anvil assembly is movable in relation to the staple cartridge between spaced and clamped positions. The anvil assembly includes a housing defining a recess and a mesh material positioned within the recess. The staple cartridge includes a body defining a plurality of staple receiving slots. Each of the staple receiving slots supports a staple. The staple receiving slots are aligned with the recess when the anvil assembly and the staple cartridge are in the clamped position such that the plurality of staples are ejected and penetrate into the mesh material when the tool assembly is fired. Each of the plurality of staples includes a backspan and a leg extending from each end of the backspan. Each of the legs includes a locking structure that is configured to mesh or interlock with the mesh material of the anvil assembly upon penetration of the mesh material by the legs of the staples to obstruct withdrawal of the legs from the locking material.

14 Claims, 9 Drawing Sheets

(51) Int. Cl.
*A61B 17/068* (2006.01)
*A61B 17/072* (2006.01)

(52) U.S. Cl.
CPC ... *A61B 17/07207* (2013.01); *A61B 17/07292* (2013.01); *A61B 2017/07228* (2013.01); *A61B 2017/07257* (2013.01); *A61B 2017/07271* (2013.01); *A61B 2017/07285* (2013.01)

(58) Field of Classification Search
CPC  A61B 2017/07228; A61B 2017/07257; A61B 2017/07271; A61B 2017/07285
USPC .................................................... 227/175.1
See application file for complete search history.

(56) References Cited

U.S. PATENT DOCUMENTS

| | | |
|---|---|---|
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,534,350 A | 8/1985 | Golden et al. |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 4,994,073 A * | 2/1991 | Green .................. A61B 17/064 411/457 |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |

(56) References Cited

U.S. PATENT DOCUMENTS

| | | | |
|---|---|---|---|
| 6,083,241 | A | 7/2000 | Longo et al. |
| 6,102,271 | A | 8/2000 | Longo et al. |
| 6,117,148 | A | 9/2000 | Ravo et al. |
| 6,119,913 | A | 9/2000 | Adams et al. |
| 6,126,058 | A | 10/2000 | Adams et al. |
| 6,142,933 | A | 11/2000 | Longo et al. |
| 6,149,667 | A | 11/2000 | Hovland et al. |
| 6,176,413 | B1 | 1/2001 | Heck et al. |
| 6,179,195 | B1 | 1/2001 | Adams et al. |
| 6,193,129 | B1 | 2/2001 | Bittner et al. |
| 6,203,553 | B1 | 3/2001 | Robertson et al. |
| 6,209,773 | B1 | 4/2001 | Bolduc et al. |
| 6,241,140 | B1 | 6/2001 | Adams et al. |
| 6,253,984 | B1 | 7/2001 | Heck et al. |
| 6,258,107 | B1 | 7/2001 | Balazs et al. |
| 6,264,086 | B1 | 7/2001 | McGuckin, Jr. |
| 6,269,997 | B1 | 8/2001 | Balazs et al. |
| 6,273,897 | B1 | 8/2001 | Dalessandro et al. |
| 6,279,809 | B1 | 8/2001 | Nicolo |
| 6,302,311 | B1 | 10/2001 | Adams et al. |
| 6,338,737 | B1 | 1/2002 | Toledano |
| 6,343,731 | B1 | 2/2002 | Adams et al. |
| 6,387,105 | B1 | 5/2002 | Gifford, III et al. |
| 6,398,795 | B1 | 6/2002 | McAlister et al. |
| 6,402,008 | B1 | 6/2002 | Lucas |
| 6,439,446 | B1 | 8/2002 | Perry et al. |
| 6,443,973 | B1 | 9/2002 | Whitman |
| 6,450,390 | B2 | 9/2002 | Heck et al. |
| 6,478,210 | B2 | 11/2002 | Adams et al. |
| 6,488,197 | B1 | 12/2002 | Whitman |
| 6,491,201 | B1 | 12/2002 | Whitman |
| 6,494,877 | B2 | 12/2002 | Odell et al. |
| 6,503,259 | B2 | 1/2003 | Huxel et al. |
| 6,517,566 | B1 | 2/2003 | Hovland et al. |
| 6,520,398 | B2 | 2/2003 | Nicolo |
| 6,533,157 | B1 | 3/2003 | Whitman |
| 6,551,334 | B2 | 4/2003 | Blatter et al. |
| 6,578,751 | B2 | 6/2003 | Hartwick |
| 6,585,144 | B2 | 7/2003 | Adams et al. |
| 6,588,643 | B2 | 7/2003 | Bolduc et al. |
| 6,592,596 | B1 | 7/2003 | Geitz |
| 6,601,749 | B2 | 8/2003 | Sullivan et al. |
| 6,605,078 | B2 | 8/2003 | Adams |
| 6,605,098 | B2 | 8/2003 | Nobis et al. |
| 6,626,921 | B2 | 9/2003 | Blatter et al. |
| 6,629,630 | B2 | 10/2003 | Adams |
| 6,631,837 | B1 | 10/2003 | Heck |
| 6,632,227 | B2 | 10/2003 | Adams |
| 6,632,237 | B2 | 10/2003 | Ben-David et al. |
| 6,652,542 | B2 | 11/2003 | Blatter et al. |
| 6,659,327 | B2 | 12/2003 | Heck et al. |
| 6,676,671 | B2 | 1/2004 | Robertson et al. |
| 6,681,979 | B2 | 1/2004 | Whitman |
| 6,685,079 | B2 | 2/2004 | Sharma et al. |
| 6,695,198 | B2 | 2/2004 | Adams et al. |
| 6,695,199 | B2 | 2/2004 | Whitman |
| 6,698,643 | B2 | 3/2004 | Whitman |
| 6,716,222 | B2 | 4/2004 | McAlister et al. |
| 6,716,233 | B1 | 4/2004 | Whitman |
| 6,726,697 | B2 | 4/2004 | Nicholas et al. |
| 6,742,692 | B2 | 6/2004 | Hartwick |
| 6,743,244 | B2 | 6/2004 | Blatter et al. |
| 6,763,993 | B2 | 7/2004 | Bolduc et al. |
| 6,769,590 | B2 | 8/2004 | Vresh et al. |
| 6,769,594 | B2 | 8/2004 | Orban, III |
| 6,820,791 | B2 | 11/2004 | Adams |
| 6,821,282 | B2 | 11/2004 | Perry et al. |
| 6,827,246 | B2 | 12/2004 | Sullivan et al. |
| 6,840,423 | B2 | 1/2005 | Adams et al. |
| 6,843,403 | B2 | 1/2005 | Whitman |
| 6,846,308 | B2 | 1/2005 | Whitman et al. |
| 6,852,122 | B2 | 2/2005 | Rush |
| 6,866,178 | B2 | 3/2005 | Adams et al. |
| 6,872,214 | B2 | 3/2005 | Sonnenschein et al. |
| 6,874,669 | B2 | 4/2005 | Adams et al. |
| 6,884,250 | B2 | 4/2005 | Monassevitch et al. |
| 6,905,504 | B1 | 6/2005 | Vargas |
| 6,938,814 | B2 | 9/2005 | Sharma et al. |
| 6,942,675 | B1 | 9/2005 | Vargas |
| 6,945,444 | B2 | 9/2005 | Gresham et al. |
| 6,953,138 | B1 | 10/2005 | Dworak et al. |
| 6,957,758 | B2 | 10/2005 | Aranyi |
| 6,959,851 | B2 | 11/2005 | Heinrich |
| 6,978,922 | B2 | 12/2005 | Bilotti et al. |
| 6,981,941 | B2 | 1/2006 | Whitman et al. |
| 6,981,979 | B2 | 1/2006 | Nicolo |
| 7,032,798 | B2 | 4/2006 | Whitman et al. |
| 7,059,331 | B2 | 6/2006 | Adams et al. |
| 7,059,510 | B2 | 6/2006 | Orban, III |
| 7,077,856 | B2 | 7/2006 | Whitman |
| 7,080,769 | B2 | 7/2006 | Vresh et al. |
| 7,086,267 | B2 | 8/2006 | Dworak et al. |
| 7,114,642 | B2 | 10/2006 | Whitman |
| 7,118,528 | B1 | 10/2006 | Piskun |
| 7,122,044 | B2 | 10/2006 | Bolduc et al. |
| 7,128,748 | B2 | 10/2006 | Mooradian et al. |
| 7,141,055 | B2 | 11/2006 | Abrams et al. |
| 7,168,604 | B2 | 1/2007 | Milliman et al. |
| 7,179,267 | B2 | 2/2007 | Nolan et al. |
| 7,182,239 | B1 | 2/2007 | Myers |
| 7,195,142 | B2 | 3/2007 | Orban, III |
| 7,207,168 | B2 | 4/2007 | Doepker et al. |
| 7,220,237 | B2 | 5/2007 | Gannoe et al. |
| 7,234,624 | B2 | 6/2007 | Gresham et al. |
| 7,235,089 | B1 | 6/2007 | McGuckin, Jr. |
| RE39,841 | E | 9/2007 | Bilotti et al. |
| 7,285,125 | B2 | 10/2007 | Viola |
| 7,303,106 | B2 | 12/2007 | Milliman et al. |
| 7,303,107 | B2 | 12/2007 | Milliman et al. |
| 7,309,341 | B2 | 12/2007 | Ortiz et al. |
| 7,322,994 | B2 | 1/2008 | Nicholas et al. |
| 7,325,713 | B2 | 2/2008 | Aranyi |
| 7,334,718 | B2 | 2/2008 | McAlister et al. |
| 7,335,212 | B2 | 2/2008 | Edoga et al. |
| 7,364,060 | B2 | 4/2008 | Milliman |
| 7,398,908 | B2 | 7/2008 | Holsten et al. |
| 7,399,305 | B2 | 7/2008 | Csiky et al. |
| 7,401,721 | B2 | 7/2008 | Holsten et al. |
| 7,401,722 | B2 | 7/2008 | Hur |
| 7,407,075 | B2 | 8/2008 | Holsten et al. |
| 7,410,086 | B2 | 8/2008 | Ortiz et al. |
| 7,422,137 | B2 | 9/2008 | Manzo |
| 7,422,138 | B2 | 9/2008 | Bilotti et al. |
| 7,431,191 | B2 | 10/2008 | Milliman |
| 7,438,718 | B2 | 10/2008 | Milliman et al. |
| 7,455,676 | B2 | 11/2008 | Holsten et al. |
| 7,455,682 | B2 | 11/2008 | Viola |
| 7,481,347 | B2 | 1/2009 | Roy |
| 7,494,038 | B2 | 2/2009 | Milliman |
| 7,506,791 | B2 | 3/2009 | Omaits et al. |
| 7,516,877 | B2 | 4/2009 | Aranyi |
| 7,527,185 | B2 | 5/2009 | Harari et al. |
| 7,537,602 | B2 | 5/2009 | Whitman |
| 7,540,839 | B2 | 6/2009 | Butler et al. |
| 7,546,939 | B2 | 6/2009 | Adams et al. |
| 7,546,940 | B2 | 6/2009 | Milliman et al. |
| 7,547,312 | B2 | 6/2009 | Bauman et al. |
| 7,556,186 | B2 | 7/2009 | Milliman |
| 7,559,451 | B2 | 7/2009 | Sharma et al. |
| 7,585,306 | B2 | 9/2009 | Abbott et al. |
| 7,588,174 | B2 | 9/2009 | Holsten et al. |
| 7,600,663 | B2 | 10/2009 | Green |
| 7,611,038 | B2 | 11/2009 | Racenet et al. |
| 7,635,385 | B2 | 12/2009 | Milliman et al. |
| 7,669,747 | B2 | 3/2010 | Weisenburgh, II et al. |
| 7,686,201 | B2 | 3/2010 | Csiky |
| 7,694,864 | B2 | 4/2010 | Okada et al. |
| 7,699,204 | B2 | 4/2010 | Viola |
| 7,708,181 | B2 | 5/2010 | Cole et al. |
| 7,717,313 | B2 | 5/2010 | Criscuolo et al. |
| 7,721,932 | B2 | 5/2010 | Cole et al. |
| 7,726,539 | B2 | 6/2010 | Holsten et al. |
| 7,743,958 | B2 | 6/2010 | Orban, III |
| 7,744,627 | B2 | 6/2010 | Orban, III et al. |

(56) References Cited

U.S. PATENT DOCUMENTS

| | | |
|---|---|---|
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,292,154 B2 * | 10/2012 | Marczyk ......... A61B 17/07207 227/176.1 |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,721,664 B2 * | 5/2014 | Ruff ................. A61B 17/11 606/139 |
| 8,733,611 B2 | 5/2014 | Milliman |
| 8,777,987 B2 * | 7/2014 | Herrmann ............ B26F 3/08 606/228 |
| 9,248,580 B2 * | 2/2016 | Leung ............... A61L 17/12 |
| 9,414,839 B2 * | 8/2016 | Penna ............. A61B 17/1155 |
| 10,188,384 B2 * | 1/2019 | Gross ................ A61F 5/566 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0260278 A1 | 11/2007 | Wheeler et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |

(56) References Cited

U.S. PATENT DOCUMENTS

| | | |
|---|---|---|
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |

FOREIGN PATENT DOCUMENTS

| | | |
|---|---|---|
| DE | 1057729 B | 5/1959 |
| DE | 3301713 A1 | 7/1984 |
| EP | 0129442 A1 | 12/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2110082 A1 | 10/2009 |
| EP | 2138118 A2 | 12/2009 |
| EP | 2168510 A1 | 3/2010 |
| EP | 2238926 A2 | 10/2010 |
| EP | 2316352 A1 | 5/2011 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |
| WO | 2011160124 A1 | 12/2011 |

* cited by examiner

SURGICAL STAPLING DEVICE

CROSS-REFERENCE TO RELATED APPLICATIONS

This application claims the benefit of and priority to U.S. Provisional Patent Application Ser. No. 62/528,556 filed Jul. 5, 2017, the entire disclosure of which is incorporated by reference herein.

BACKGROUND

1. Technical Description

The present disclosure is directed to circular stapling devices and, more particularly, to circular stapling devices that include non-deformable staples and do not require precisely formed staple deforming pockets.

2. Background of Related Art

Circular stapling devices are commonly used to perform anastomosis procedures to join two tubular tissue sections. Typically, a circular stapling device includes a shell assembly having a staple cartridge that defines a plurality of staple receiving pockets that support an annular array of staples, and an anvil assembly that includes a staple deforming surface that defines an annular array of staple deforming pockets. During staple formation, the staple pockets must be aligned with the staple deforming pockets to properly form the staples and create a leak free staple line in the tissue sections. Post-surgical staple line leaks can result in infection and even death.

In known circular stapling devices, the anvil assembly includes an anvil center rod that supports splines. The shell assembly includes a shell housing that also includes splines that receive the splines on the anvil center rod to properly align the staple receiving pockets of the staple cartridge with the staple deforming pockets on the anvil assembly. However, the splines on the anvil center rod and/or the shell housing may become damaged such that the staple receiving pockets of the staple cartridge and the staple deforming pockets on the anvil assembly are not properly aligned. Damage to the splines may be caused by "crashing" which occurs when the splines on the anvil center rod engage the splines on the shell housing head on such that some of the splines fracture.

A continuing need in the stapling arts exists for a circular stapling device that does not require alignment between the staple receiving pockets of the staple cartridge and the staple deforming pockets on the anvil assembly to facilitate proper staple formation.

SUMMARY

One aspect of the present disclosure is directed to a circular stapling device including a handle assembly, a body portion, and a tool assembly. The body portion has a proximal portion and a distal portion. The proximal portion of the body portion is connected to the handle assembly. The tool assembly is supported on the distal portion of the body portion and includes an anvil assembly and a shell assembly. The anvil assembly includes a center rod and an anvil head assembly. The center rod has a proximal portion and a distal portion. The anvil head assembly is secured to the distal portion of the center rod and includes a housing defining an outer annular recess and a locking material positioned within the outer annular recess. The shell assembly includes a shell housing and a staple cartridge. The staple cartridge supports a plurality of staples that are axially aligned with the outer annular recess. Each of the plurality of staples includes a backspan and a leg extending from each end of the backspan. Each of the legs includes a locking structure that is configured to engage the locking material of the anvil head assembly upon penetration of the locking material by the legs of the staples to obstruct withdrawal of the legs from within the locking material.

Another aspect of the present disclosure is directed to an anvil assembly including a center rod and an anvil head assembly. The center rod includes a proximal portion and a distal portion. The anvil head assembly includes a central post, a housing, a cut ring, and a locking material. The central post is secured to the distal portion of the center rod. The housing defines an outer annular recess and an inner annular recess that are positioned about the central post. The locking material is positioned within the outer annular recess and the cut ring is positioned within the inner annular recess.

In embodiments, the locking material includes a mesh material.

In some embodiments, the anvil head assembly includes a reinforcement material positioned over the locking material proximally of the mesh material.

In certain embodiments, the housing includes a proximally facing surface that defines the outer annular recess and the reinforcement material is positioned on the proximally facing surface over the locking material.

In embodiments, the locking structure includes teeth positioned along at least a portion of the legs of the plurality of staples.

In some embodiments, each of the legs defines a longitudinal axis and the teeth on each of the legs include a distal surface that defines an acute angle with the longitudinal axis of the legs. The distal surface of the teeth extends outwardly from the longitudinal axis in a proximal direction.

In certain embodiments, the teeth on each of the legs include a proximal surface that is configured to engage the mesh material when the legs of the plurality of staples penetrate the mesh material to prevent withdrawal of the legs from the mesh material.

In embodiments, the proximal surface of each of the teeth is perpendicular to the longitudinal axis of the legs.

In some embodiments, the housing of the anvil head assembly defines an inner annular recess that is positioned within the outer annular recess and the stapling device further includes a cut ring that is supported within the inner annular recess.

In certain embodiments, the anvil head assembly is pivotally secured to the center rod.

In embodiments, the stapling device further includes a handle assembly and a body portion extending from the handle assembly having a distal portion, wherein the tool assembly is supported on the distal portion of the body portion.

Another aspect of the present disclosure is directed to a tool assembly including an anvil assembly and a staple cartridge. The anvil assembly is movable in relation to the staple cartridge between spaced and clamped positions. The anvil assembly includes a housing defining a recess and a locking material positioned within the recess. The staple cartridge includes a body defining a plurality of staple receiving slots. Each of the staple receiving slots supports a staple of the plurality of staples. The staple receiving slots are aligned with the recess when the anvil assembly and the staple cartridge are in the clamped position such that the plurality of staples are ejected and penetrate into the mesh material when the tool assembly is fired. Each of the plurality of staples includes a backspan and a leg extending from each end of the backspan. Each of the legs includes locking structure that is configured to engage the mesh material of the anvil assembly upon penetration of the mesh material by the legs of the staples to obstruct withdrawal of the legs from the locking material.

BRIEF DESCRIPTION OF THE DRAWINGS

Various embodiments of the presently disclosed circular stapling device and non-deformable staples are described herein below with reference to the drawings, wherein.

DETAILED DESCRIPTION OF EMBODIMENTS

Figure 1:
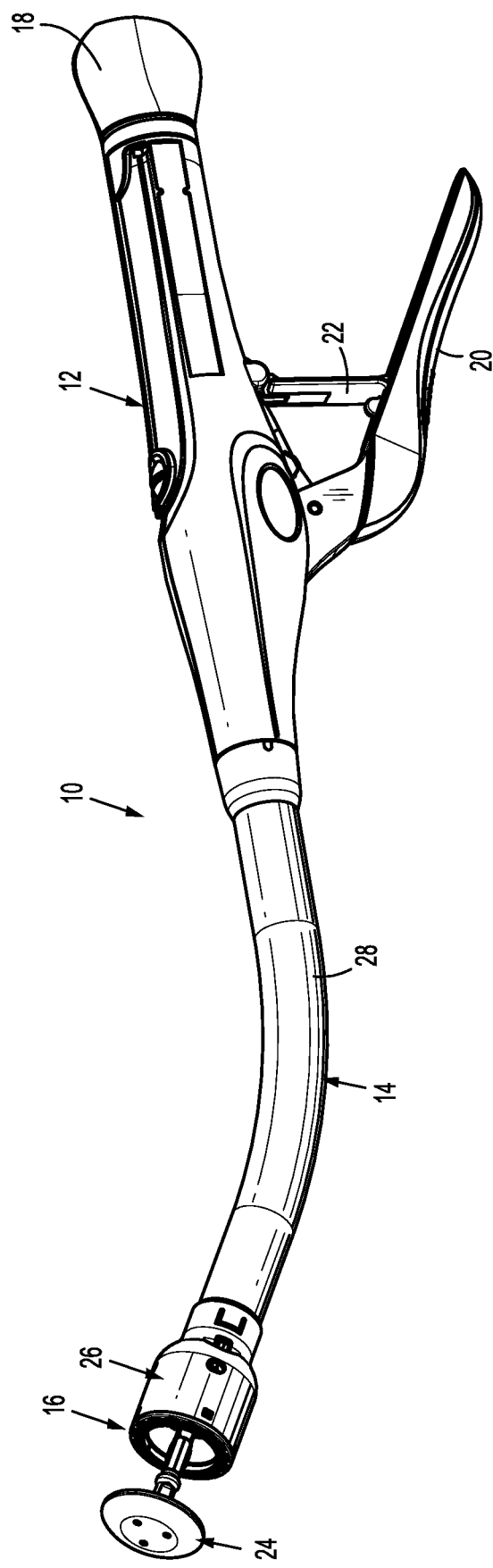
FIG. 1 is a side perspective view of one exemplary embodiment of the presently disclosed circular stapling device with an anvil assembly and a shell assembly in a spaced position.

The presently disclosed circular stapling device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel.

The presently disclosed circular stapling device includes an anvil assembly and a shell assembly. The anvil assembly includes an anvil head that defines an outer annular recess that supports a locking material. The shell assembly includes a staple cartridge that supports an annular array of staples that are aligned with the outer annular recess of the anvil head. Each of the staples of the annular array of staples includes a backspan and a leg extending from each end of the backspan. The legs have locking structure that is configured to facilitate passage of the legs of the staples through tissue and into locking engagement with the locking material. In embodiments, the locking structure includes a plurality of teeth although other locking structures may be used. When the circular stapling device is fired, the staples are ejected from the staple cartridge and pass through tissue and into the locking material. The teeth engage the locking material to prevent the legs of the staples from withdrawing from the tissue. By providing an annular ring of locking material that is aligned with annular array of staples obviates the need to properly align the staple cartridge with the anvil head prior to firing the staples from the staple cartridge.

Figure 2:
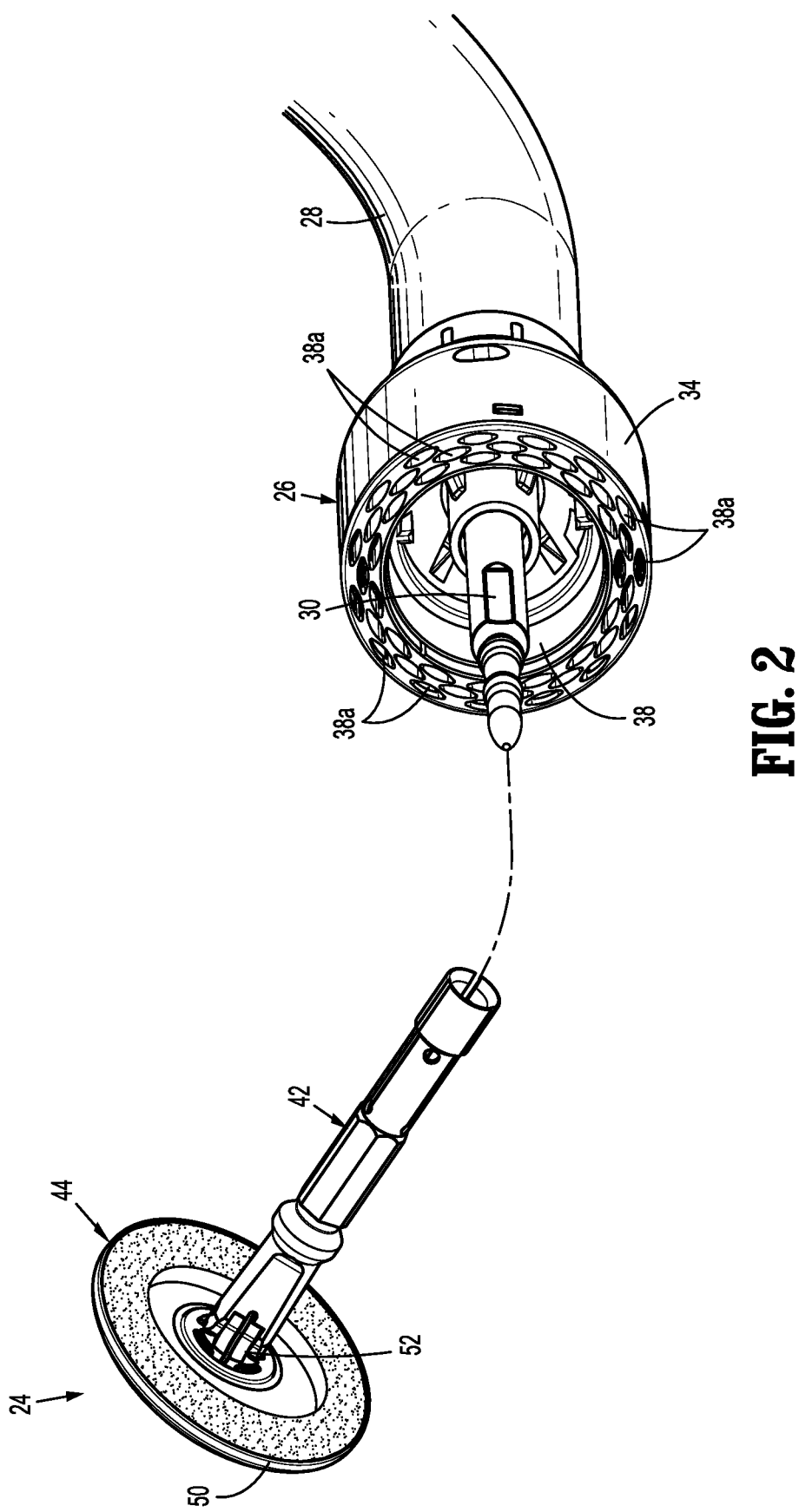
FIG. 2 is an enlarged side perspective view of the distal end of the circular stapling device shown in FIG. 1 with the anvil assembly separated from an anvil retainer of the circular stapling device.

FIGS. 1 and 2 illustrate one exemplary embodiment of the presently disclosed surgical stapling device shown generally as stapling device 10. Stapling device 10 includes a handle assembly 12, a body portion 14, and a tool assembly 16. The handle assembly 12 includes an approximation knob 18, a firing trigger 20, and a trigger lockout 22. The tool assembly 16 includes an anvil assembly 24 and a shell assembly 26. The body portion 14 has a proximal end supported on the handle assembly 12 and a distal end that supports the tool assembly 16. The body portion 14 includes a tubular housing 28 and an anvil retainer 30 (FIG. 2). The tubular housing 28 supports the shell assembly 26 and the anvil retainer 30 (FIG. 2) extends through the tubular housing 28 and the shell assembly 26 of the tool assembly 16 and supports the anvil assembly 24. The anvil retainer 30 is movable within the body portion 14 to move the anvil assembly 24 in relation to the shell assembly 26 between spaced (FIG. 1) and clamped (FIG. 11) positions.

U.S. Pat. No. 9,492,168 ("the '168 patent") and U.S. Patent Publication No. 2015/0351769 disclose manually operated surgical stapling devices including the components identified above. Both of these documents are incorporated herein by reference in their entirety. Although FIG. 1 illustrates a manually operated stapling device, it is envisioned that the stapling device 10 could also be electrically powered or configured for attachment to a robotically controlled system. U.S. Publication Nos. 2015/0014392 and 2015/0048140 describe electrically powered surgical stapling devices and are incorporated herein in their entirety by reference.

Figure 3:
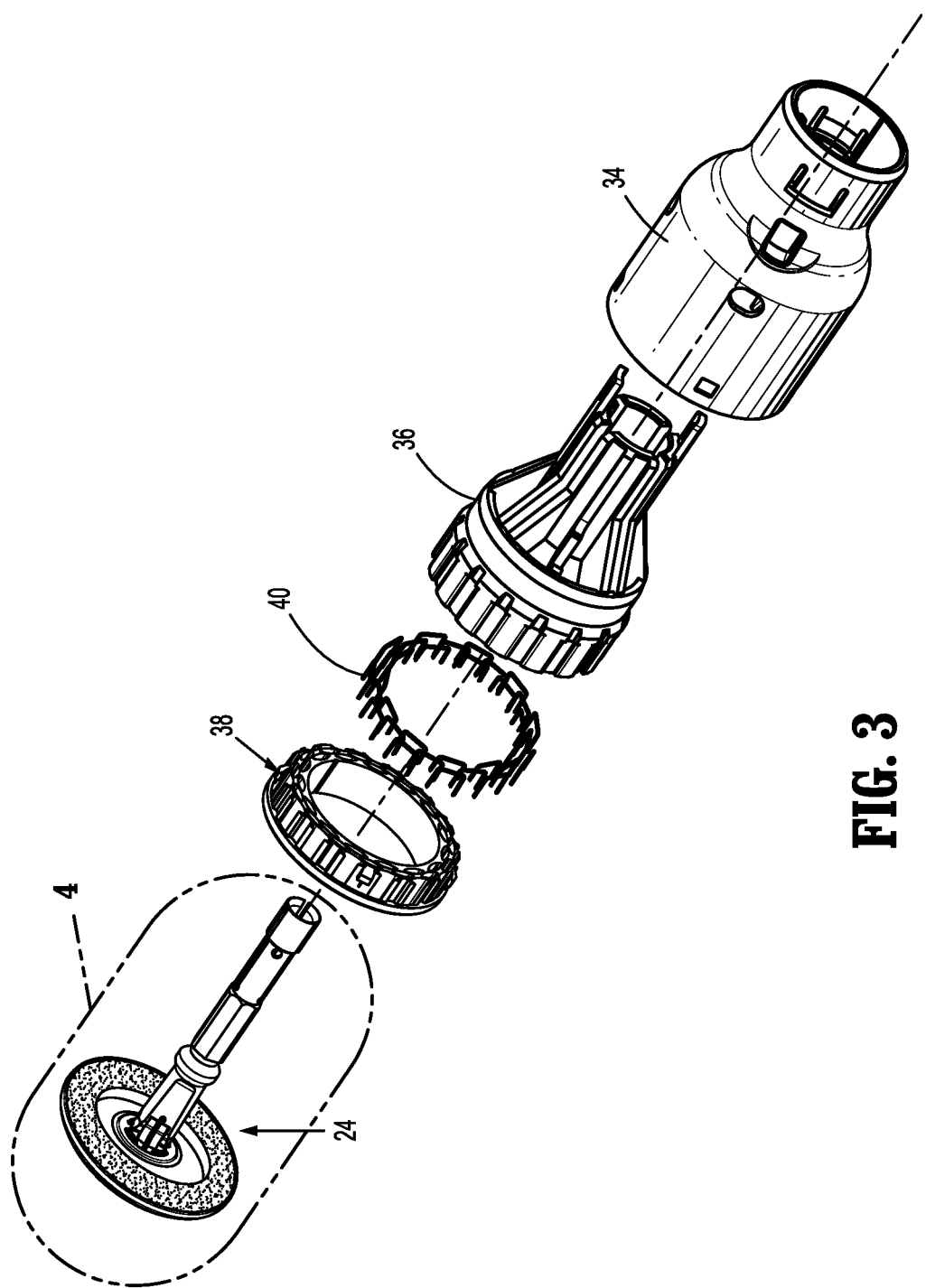
FIG. 3 is a side, perspective, exploded view of the anvil assembly and the shell assembly of the circular stapling device shown in FIG. 1.
Figure 4:
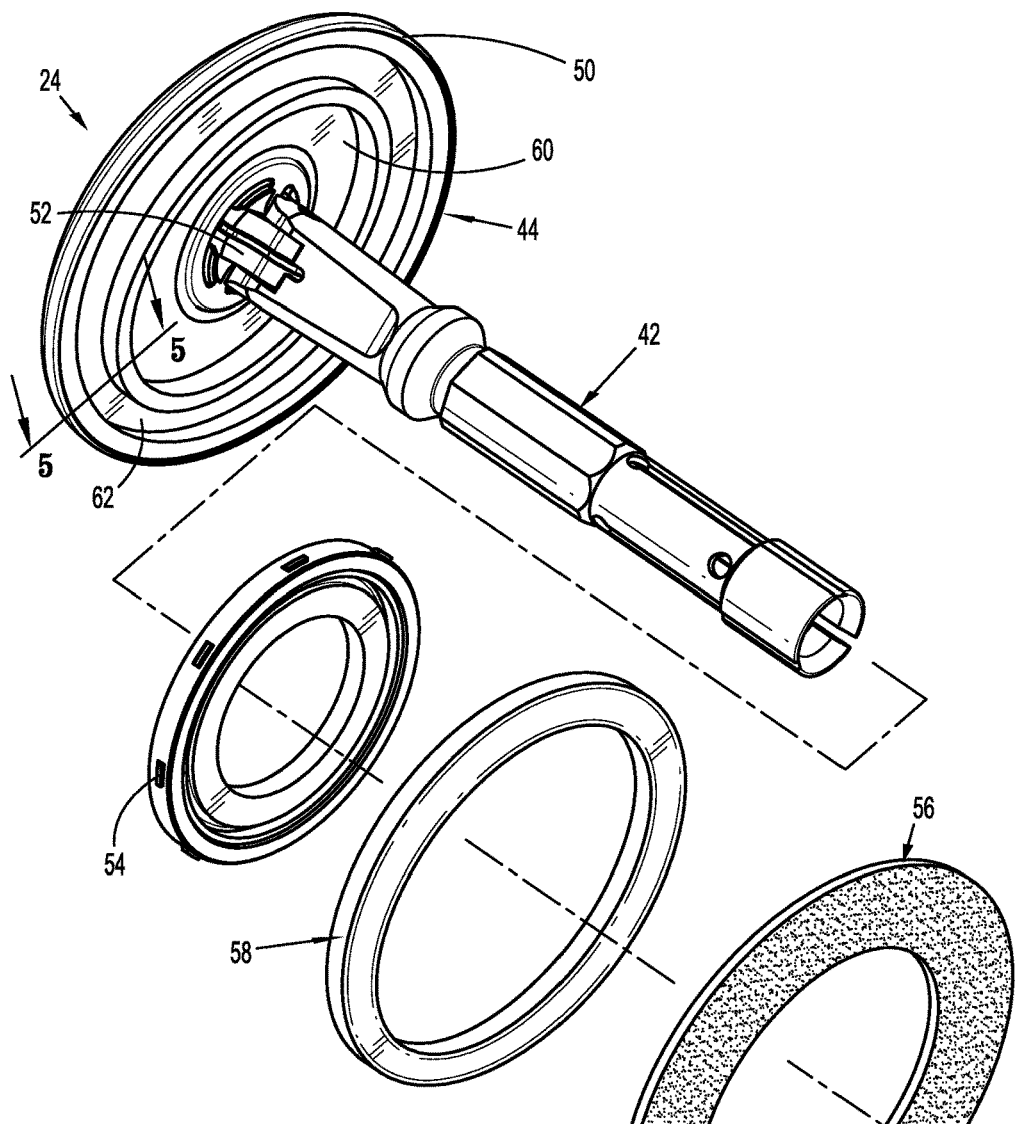
FIG. 4 is an enlarged view of the indicated area of detail shown in FIG. 3.
Figure 5:
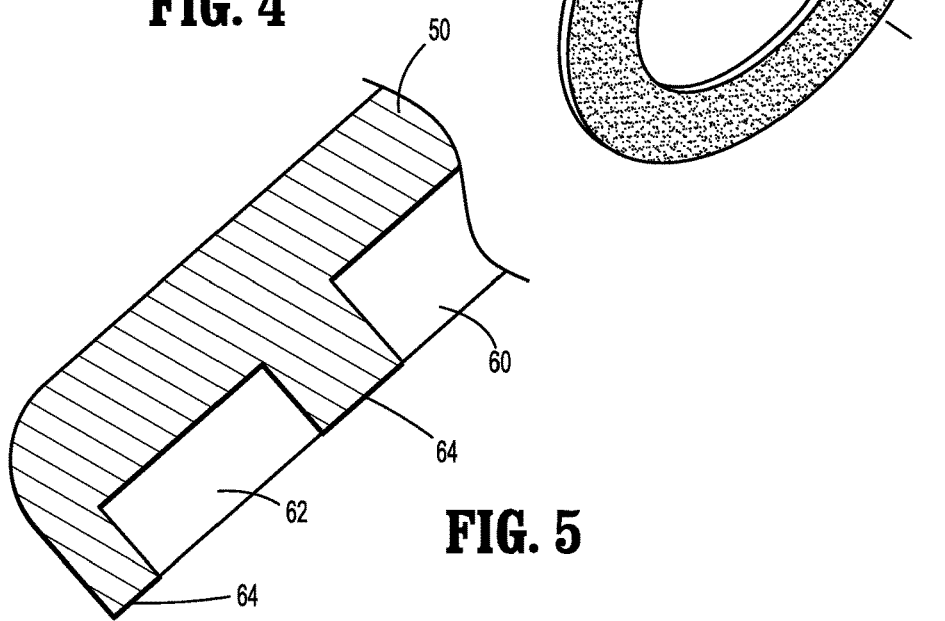
FIG. 5 is a cross-sectional view taken along section line 5-5 of FIG. 4.
Figure 6:
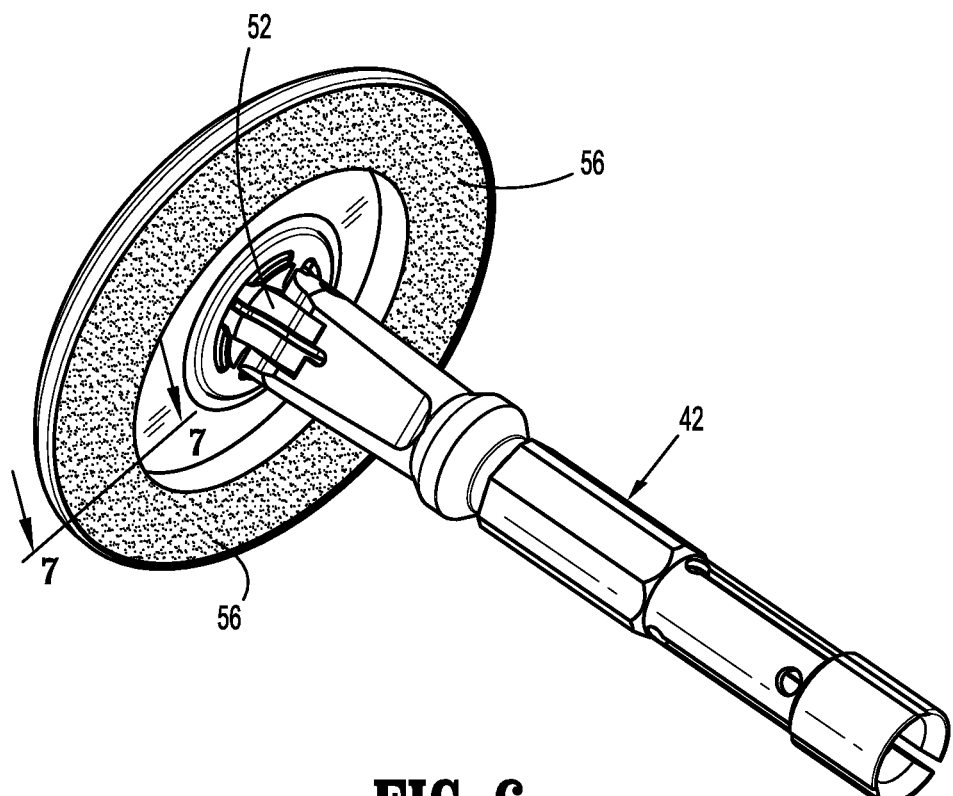
FIG. 6 is a side perspective view from the proximal end of the anvil assembly of the circular stapling device shown in FIG. 1.
Figure 7:
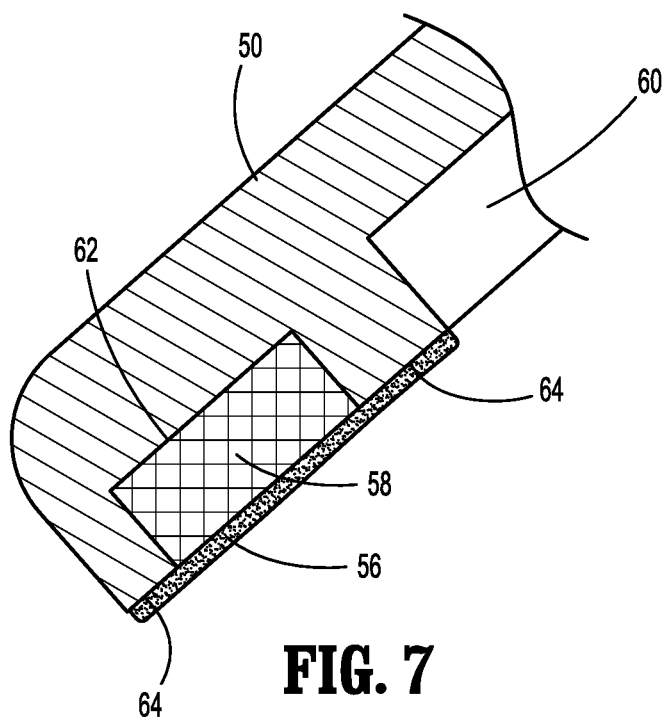
FIG. 7 is a cross-sectional view taken along section line 7-7 of FIG. 6.
Figure 12:
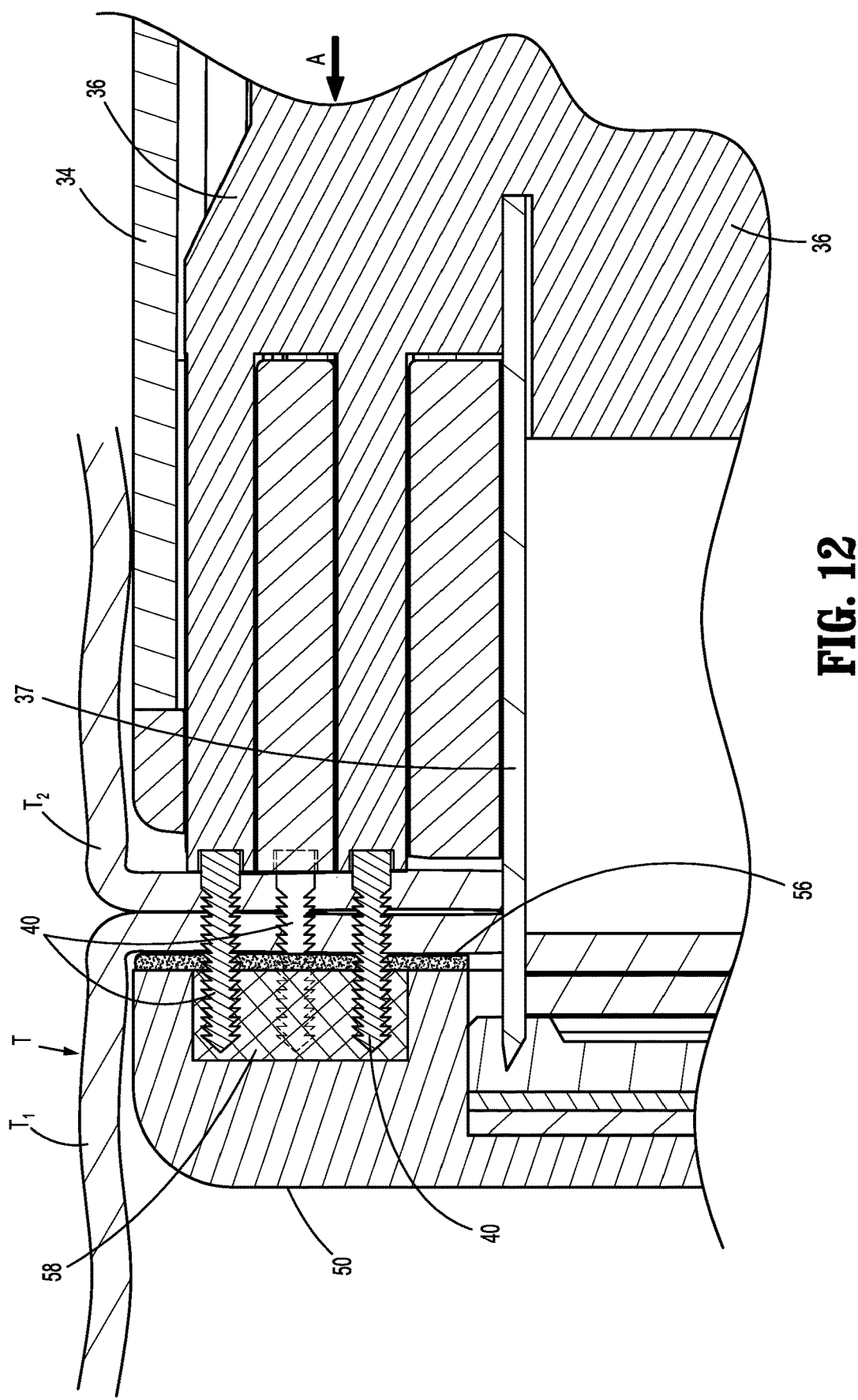
FIG. 12 is a cross-sectional view taken along section line 12-12 of FIG. 11.
Figure 13:
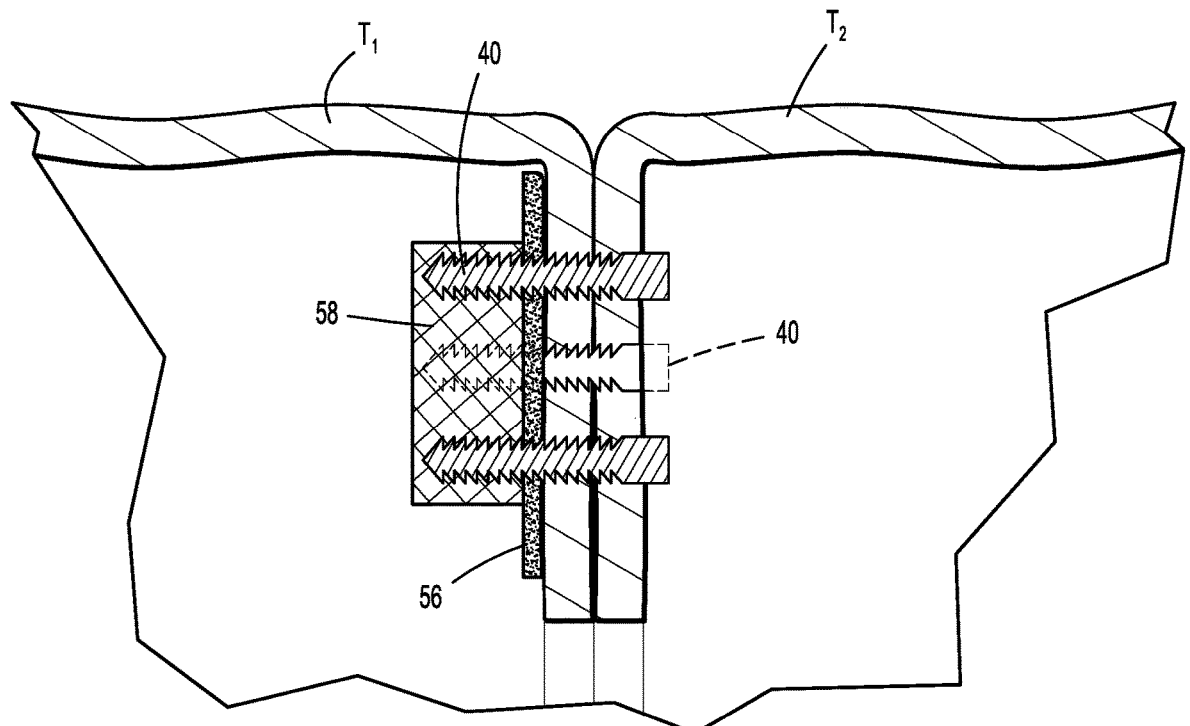
FIG. 13 is a side, cross-sectional view taken through tissue sections after the circular stapling device has been fired to position the staples through the tissue sections.
Figure 14:
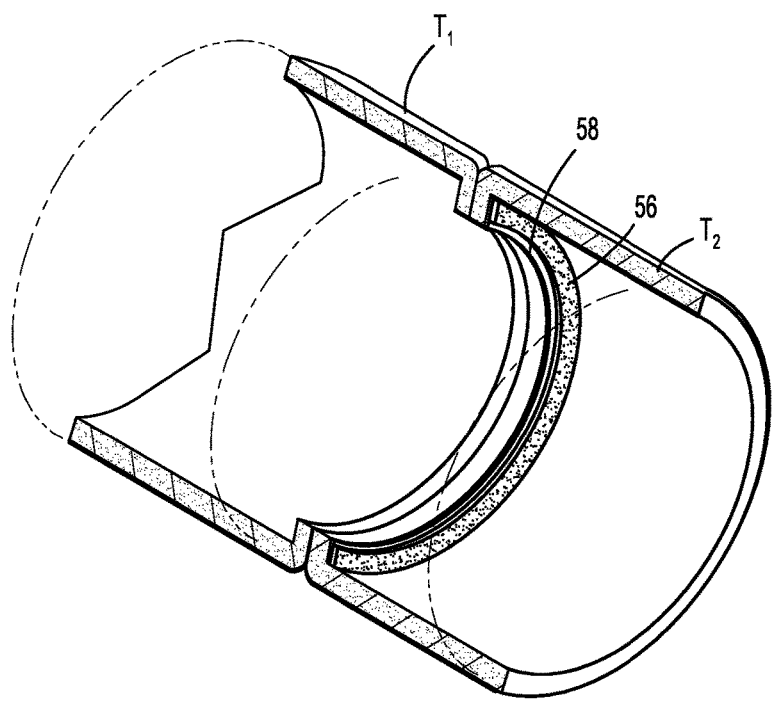
FIG. 14 is a side, cross-sectional view taken through the tissue sections after the anastomosis has been performed.

Referring to FIGS. 2 and 3, the shell assembly 26 includes a shell housing 34, a pusher 36, an annular knife 37 (FIG. 12), a staple cartridge 38, and a plurality of staples 40. The staple cartridge 38 is supported in a distal portion of the shell housing 34 and defines an annular array of staple receiving pockets 38a. Each of the staple receiving pockets 38a supports a staple 40 (FIG. 3). For a more detailed description of the shell assembly, see the '168 patent.

Referring also to FIGS. 4-7, the anvil assembly 24 includes an anvil center rod 42 and an anvil head assembly 44. The anvil center rod 42 has a proximal portion that is configured to be releasably coupled to the anvil retainer 30 (FIG. 2) and a distal portion. In some embodiments, the anvil head assembly 44 is pivotally supported on the distal portion of the anvil center rod 42 by a pivot member 45. Alternately, the anvil head assembly 44 can be fixedly mounted to the anvil center rod 42.

The anvil head assembly 24 includes a housing 50, a post 52 that is secured to or formed integrally with the housing 50, a cut ring 54, a reinforcement material 56, and a locking material 58. The housing 50 defines an inner annular recess 60, an outer annular recess 62, and a proximally facing support surface 64. The inner annular recess 60 is positioned about the post 52 and receives the cut ring 54 such that the cut ring 54 is positioned to engage the annular knife 37 (FIG. 12) of the shell assembly 26 when the stapling device 10 is fired. As is known in the art, the cut ring 54 may be formed from a variety of different materials and have one or more layers of material. The outer annular recess 62 is positioned radially outward of the inner annular recess 60 at a location to receive the staples 40 from the staple cartridge 38 when the stapling device 10 is fired. The locking material 58 is positioned within the outer annular recess 62 to receive the staples 40 as discussed in further detail below. The reinforcement material 56 is supported on the proximally facing surface 64 of the housing 50 and extends over the outer annular recess 62 and the locking material 58. In embodiments, the reinforcement material 56 is secured to the proximally facing surface of the housing 50 using an adhesive although other means of attachment are envisioned.

The locking material 58 is formed from a biocompatible substrate which is a bioabsorbable, non-absorbable, natural, or synthetic material that is configured to mesh or interlock with the staples 40 to prevent withdrawal of the staples from the locking material. In embodiments, the locking material 58 is formed from a biocompatible mesh. Alternately, other materials that have the requisite characteristics can be also be used as the locking material.

In embodiments, the reinforcement material 56 may be fabricated from a biocompatible substrate material which is a bioabsorbable, non-absorbable, natural, synthetic, woven or unwoven material. For example, the reinforcement material can be formed of poly(lactic acid), poly(glycolic acid), poly(trimethylene carbonate), poly(dioxanone), poly(hydroxybutyrate), poly(phosphazine), polyethylene terephthalate, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes, and copolymers, block copolymers, homopolymers, blends and combinations thereof. In some embodiments, the reinforcement material 56 is formed from a bio-absorbable polyglycolic acid (PGA).

Figure 8:
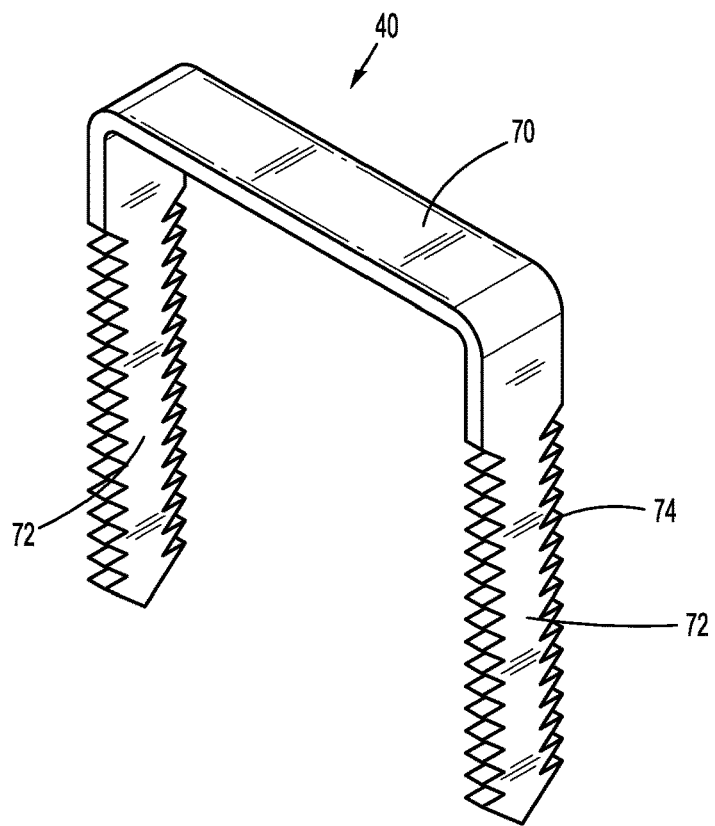
FIG. 8 is a side perspective view of a staple of the circular stapling device shown in FIG. 1.
Figure 9:
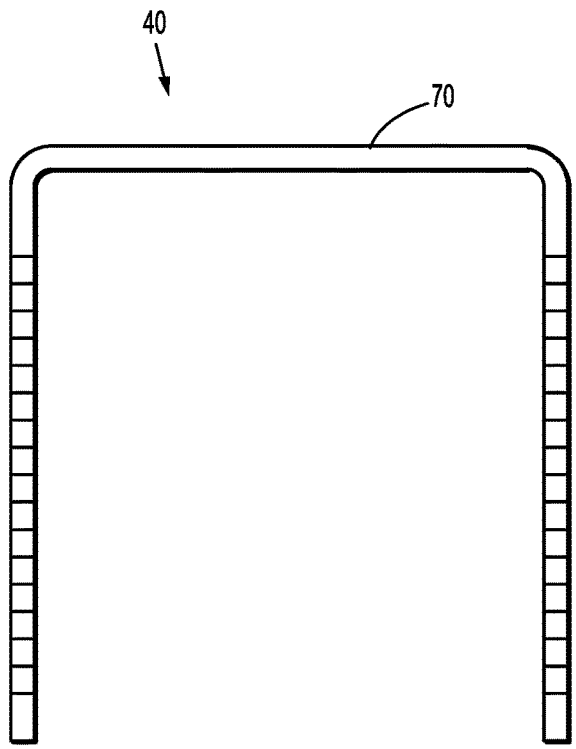
FIG. 9 is a front view of the staple shown in FIG. 8.
Figure 10:
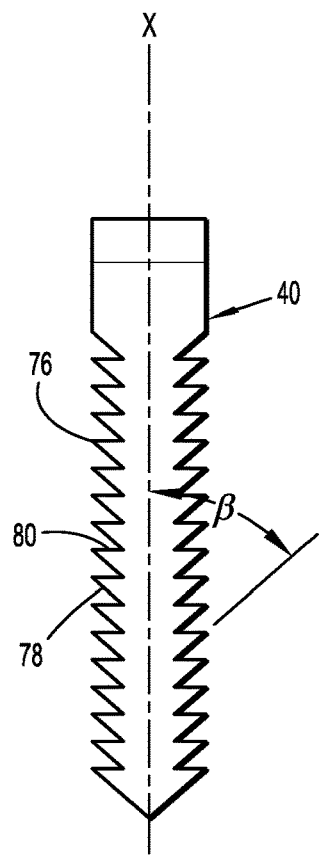
FIG. 10 is a side view of the staple shown in FIG. 8.

Referring to FIGS. 8-10, each of the staples 40 includes a backspan 70 and spaced legs 72 that extend from opposite ends of the backspan 70. At least one of the spaced legs 72 includes locking structure 74 that is configured to facilitate passage of the legs 72 through tissue "T" (FIG. 11) and the reinforcement material 56 and into the locking material 58 while obstructing removal of the legs 72 from the locking material 58. In embodiments, each of the legs 72 includes locking structure 74.

In embodiments, the locking structure 74 includes angled teeth 76 that are configured to allow passage of the legs 72 through tissue and the reinforcement material 56 into the locking material 58 while obstructing withdrawal of the legs 72 from the locking material. In embodiments, the teeth 76 are positioned along a portion of the length of the legs 72 of the staples 40 and are defined by a distal surface 78 that defines an acute angle β with a longitudinal axis "X" of the staple leg 72 and a proximal surface 80 that is configured to mesh of interlock with the locking material. The distal surface 78 tapers outwardly in the proximal direction to allow the staple legs 72 to penetrate tissue. In some embodiments, the proximal surface 80 is substantially perpendicular to the longitudinal axis "X" of the staple leg 72. However, it is envisioned that the proximal surface 80 can define any angle that can mesh or interlock with the locking material 58 to obstruct withdrawal of the staples 40 from the locking material 58.

Figure 11:
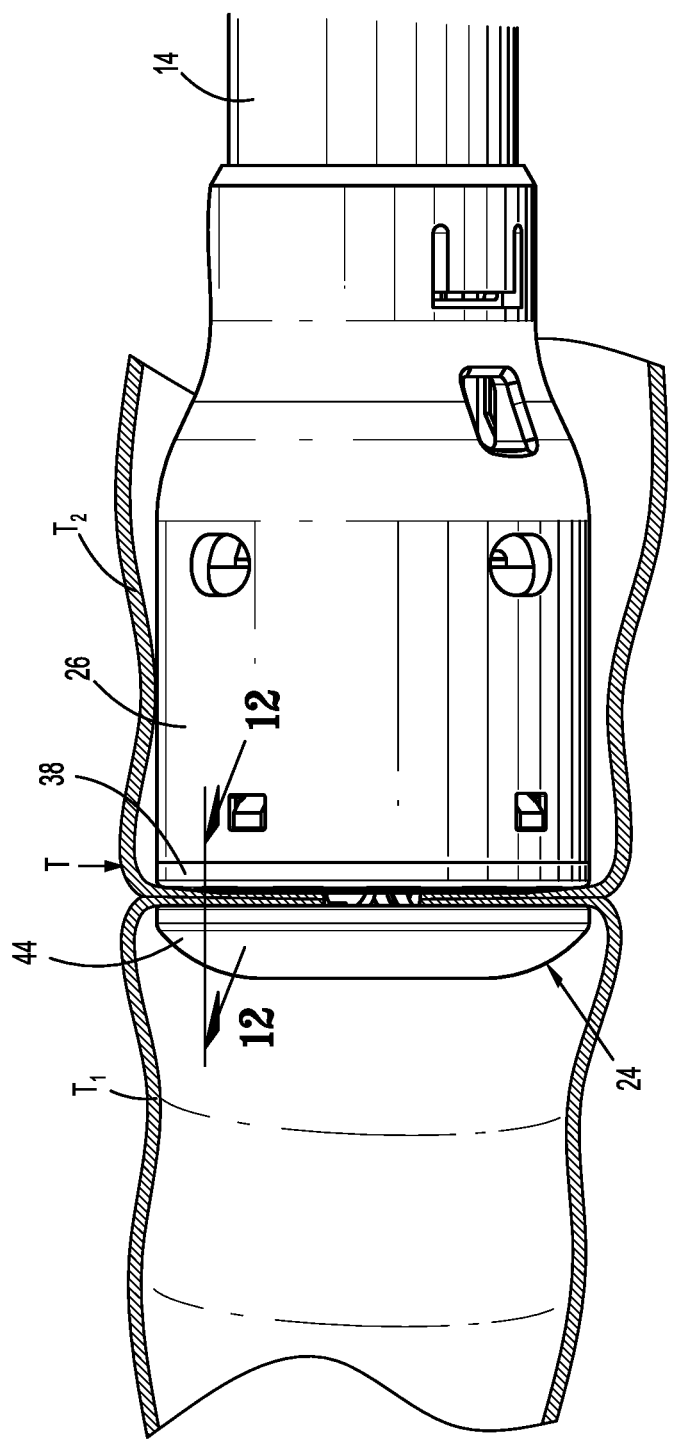
FIG. 11 is a side view of the distal end of the circular stapling device shown in FIG. 1 with the anvil assembly and the shell assembly in a clamped position about tissue after firing of the circular stapling device.

It is envisioned that the locking structure 74 may assume a variety of configurations that allow the legs 72 of the staples 40 to penetrate tissue while resisting withdrawal of the staple legs 72 from tissue "T" (FIG. 11).

Referring to FIGS. 11-14, in use of the circular stapling device 10, the tool assembly 16 of the circular stapling device 10 is positioned within tissue "T" and the anvil assembly 24 is moved in relation to the shell assembly 26 to the clamped position to clamp the tissue "T" between the staple cartridge 38 and the housing 50 of the anvil head assembly 24. More specifically, the tissue "T" includes a first tubular tissue section "T1" and a second tissue section "T2". Ends of the tissue sections "T1" and "T2" to be joined are clamped between the staple cartridge 38 and the housing 50 of the anvil head assembly 24. When the stapling device 10 is fired to advance the pusher 36 in the direction indicated by arrow "A" in FIG. 12, the staples are advanced through the tissue sections "T1" and "T2", through the reinforcement material 56 and into the locking material 58. When the locking structure 74 on the legs 72 of the staples 40 penetrates into the locking material 58, the locking material 58 meshes or interlocks with the locking structure 74 on the staple legs 72 to obstruct withdrawal of the staple legs 72 from the locking material 58 and, thus, from the tissue sections "T1" and "T2". As such, the need to properly align the staple cartridge 38 with the anvil assembly 24 to properly form the staples 40 is no longer required. In addition, by incorporating the locking material 58 into the anvil head assembly 44, deformation of the staples 40 is also not required. As such, the firing forces for firing the stapling device 10 are minimized. As illustrated, when the stapling device 10 is fired, the knife 37 is advanced to core tissue between the tissue sections "T1" and "T2".

Although the present disclosure is directed to circular stapling devices, it is envisioned that the present disclosure may be incorporated into a variety of different types of stapling devices including endoscopic and open linear and curved stapling devices, stapling devices with sequentially fired staples, and stapling devices with concurrently fired staples, and stapling devices with individually fired staples.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A circular stapling device comprising:
a handle assembly;
a body portion having a proximal portion and a distal portion, the proximal portion of the body portion being connected to the handle assembly; and
a tool assembly supported on the distal portion of the body portion, the tool assembly including an anvil assembly and a shell assembly, the anvil assembly including a center rod and an anvil head assembly, the center rod having a proximal portion and a distal portion, the anvil head assembly being secured to the distal portion of the center rod and including a housing defining an outer annular recess, and a locking material positioned within the outer annular recess, the shell assembly including a shell housing and a staple cartridge, the staple cartridge supporting a plurality of staples that are axially aligned with the annular recess, each of the plurality of staples including a backspan and a leg extending from each end of the backspan, at least one of the legs including locking structure, the locking structure being configured to engage the locking material of the anvil head assembly upon penetration of the locking material by the legs of the staples to obstruct withdrawal of the legs from the locking material;
wherein the locking material includes a mesh material and the anvil head assembly includes a reinforcement material positioned over the locking material proximally of the mesh material.

2. The circular stapling device of claim 1, wherein the housing includes a proximally facing surface that defines the outer annular recess, the reinforcement material is positioned on the proximally facing surface over the locking material.

3. The circular stapling device of claim 1, wherein the locking structure includes teeth positioned along at least a portion of the at least one leg of the plurality of staples.

4. The circular stapling device of claim 3, wherein each of the legs define a longitudinal axis and the teeth on each of the legs include a distal surface that defines an acute angle with the longitudinal axis of the legs, the distal surface of the teeth extending outwardly from the longitudinal axis in a proximal direction.

5. The circular stapling device of claim 4, wherein the teeth on the at least one leg includes a proximal surface that is configured to engage the mesh material when the at least one leg of the plurality of staples penetrates the mesh material to prevent withdrawal of the legs from the mesh material.

6. The circular stapling device of claim 5, wherein the proximal surface of each of the teeth is perpendicular to the longitudinal axis of the legs.

7. The circular stapling device of claim 1, further including a cut ring, wherein the housing of the anvil head assembly defines an inner annular recess that is positioned within the outer annular recess and the cut ring is supported within the inner annular recess.

8. The circular stapling device of claim 1, wherein the anvil head assembly is pivotally secured to the center rod.

9. The circular stapling device of claim 1, further including a handle assembly and a body portion extending from the handle assembly, the body portion having a distal portion, the tool assembly being supported on the distal portion of the body portion.

10. An anvil assembly comprising:
a center rod having a proximal portion and a distal portion; and
an anvil head assembly including a central post, a housing, a cut ring, and a locking material, the central post being secured to the distal portion of the center rod, the housing defining an outer annular recess and an inner annular recess about the central post, the locking material positioned within the outer annular recess and the cut ring being positioned within the inner annular recess;
wherein the locking material includes a mesh material and the anvil head assembly includes a reinforcement material positioned over the locking material proximally of the mesh material.

11. The anvil assembly of claim 10, wherein the housing includes a proximally facing surface that defines the outer annular recess, the reinforcement material is positioned on the proximally facing surface over the locking material.

12. A tool assembly comprising:
an anvil assembly and a staple cartridge, the anvil assembly being movable in relation to the staple cartridge between spaced and clamped positions, the anvil assembly including a housing defining a recess and a locking material positioned within the recess, the staple cartridge including a body defining a plurality of staple receiving slots, each of the staple receiving slots supporting a staple, the staple receiving slots being aligned with the recess when the anvil assembly and the staple cartridge are in the clamped position such that the staples are ejected and penetrate into the locking material when the tool assembly is fired, each of the plurality of staples including a backspan and a leg extending from each end of the backspan, at least one of the legs including locking structure that is configured to engage the locking material of the anvil assembly upon penetration of the locking material by at least one leg of the staples to obstruct withdrawal of the legs from the locking material;
wherein the locking material includes a mesh material and the anvil head assembly includes a reinforcement material positioned over the locking material proximally of the mesh material.

13. The tool assembly of claim 12, wherein the housing includes a proximally facing surface that defines the outer annular recess and the reinforcement material is positioned on the proximally facing surface over the locking material.

14. The tool assembly of claim 12, wherein the locking structure includes teeth positioned along at least a portion of the at least one leg of the plurality of staples.

* * * * *